(12) United States Patent
Consigny et al.

(10) Patent No.: US 8,518,100 B2
(45) Date of Patent: Aug. 27, 2013

(54) DRUG ELUTING STENT FOR THE TREATMENT OF DIALYSIS GRAFT STENOSES

(75) Inventors: Paul Consigny, San Jose, CA (US); Tracey Krausa, San Francisco, CA (US); Matthew C. Merkert, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 599 days.

(21) Appl. No.: 11/312,159

(22) Filed: Dec. 19, 2005

(65) Prior Publication Data

US 2007/0142897 A1 Jun. 21, 2007

(51) Int. Cl.
*A61F 2/06* (2006.01)

(52) U.S. Cl.
USPC ................................ 623/1.15; 623/1.46

(58) Field of Classification Search
USPC .............. 623/1.15, 1.4, 1.42, 1.43, 1.39, 1.46
See application file for complete search history.

(56) References Cited

U.S. PATENT DOCUMENTS

| | | | |
|---|---|---|---|
| 5,591,226 A | 1/1997 | Trerotola | |
| 5,755,775 A | 5/1998 | Trerotola | |
| 5,827,321 A * | 10/1998 | Roubin et al. | 623/1.16 |
| 5,951,599 A * | 9/1999 | McCrory | 606/108 |
| 2004/0015180 A1 | 1/2004 | Yencho | |
| 2004/0093065 A1* | 5/2004 | Yachia et al. | 623/1.13 |
| 2004/0102836 A1* | 5/2004 | Fischell et al. | 623/1.15 |
| 2004/0102838 A1 | 5/2004 | Killion et al. | |
| 2004/0138737 A1* | 7/2004 | Davidson et al. | 623/1.35 |
| 2004/0243216 A1 | 12/2004 | Gregorich | |
| 2005/0060017 A1* | 3/2005 | Fischell et al. | 623/1.11 |
| 2005/0131458 A1* | 6/2005 | Batich et al. | 606/214 |
| 2005/0267568 A1* | 12/2005 | Berez et al. | 623/1.35 |
| 2006/0085062 A1* | 4/2006 | Lee et al. | 623/1.39 |
| 2006/0206201 A1* | 9/2006 | Garcia et al. | 623/1.51 |

FOREIGN PATENT DOCUMENTS

WO    WO 98/34668    8/1998

OTHER PUBLICATIONS

International Search Report for PCT/US2006/048152, filed Dec. 15, 2005, mailed Aug. 7, 2007, 17 pgs.
Lane et al., "Puncture-induced Deformity of a Metallic Stent within a Dialysis Access Graft Causing Thrombotic Failure: Case Report and Description of Salvage", JVIR vol. 9, No. 5, pp. 837-839 (1998).
Rhodes et al.,"Dialysis Needle Puncture of Wallgrafts Placed in Polytetrafluoroethylene Hemodialysis Grafts", JVIR vol. 16, No. 8, pp. 1129-1134 (2005).
Zaleski et al., "Metallic Stents Deployed in Synthetic Arteriovenous Hemodialysis Grafts", AJR vol. 176, pp. 1515-1519 (2000).

* cited by examiner

*Primary Examiner* — Thomas McEvoy
(74) *Attorney, Agent, or Firm* — Squire Sanders (US) LLP (57) ABSTRACT

A drug-eluting stent having a first cell pattern at one end and a second cell pattern on an opposite end. The cells in the first cell pattern have a smaller MCUSA than those in the second cell pattern. An anti-restonic drug can be coated on the first cell pattern and an anti-thrombotic drug on the second, with the anti-thrombotic drug overlaying and covering both the first and second cell patterns. The stent is operatively positionable at a distal graft-vein anastomosis with the first cell pattern adjacent the stenosis, and with the second cell pattern positioned adjacent the vein or the graft.

24 Claims, 4 Drawing Sheets

DRUG ELUTING STENT FOR THE TREATMENT OF DIALYSIS GRAFT STENOSES

BACKGROUND OF THE INVENTION

In the late stages of kidney disease it is often necessary for patients to repeatedly undergo dialysis where their blood is removed, cleansed in a dialysis machine and then returned to their bloodstream. Since arteries cannot be punctured numerous times during a dialysis process and remain functional, grafts are used. The grafts are implanted just below the patient's skin, typically on the patient's arm, to give the physician easy access to the artery and vein and the circulating blood. The graft can be easily palpated and punctured easily with needles so that the dialysis technician can access the patient's bloodstream.

Unfortunately, these grafts do not last long since they develop thrombosis and restenosis, particularly at the distal anastamosis. Wherever a graft is inserted, an injury repair process occurs, typically at the distal anastamosis where there is initially some thrombosis forming a matrix deposit. The cells migrate into that area, and the patient ends up developing a restenosis at the distal anastamosis. This stenosis developing in the distal anastamosis restricts the flow of blood flow through the graft. A blood clot will form proximal to that stenosis. The physician will usually then remove the blood clot from the graft with a balloon and then dilate the stenosis. The graft will stay open for awhile but the restenosis and rethrombosis process will reoccur, with the time interval between successive stenoses being shorter and shorter. After a few stenoses, the graft is considered a failure, requiring that the physician close the graft down and create a new one. Unfortunately, patients only have a limited number of sites where these grafts can be placed.

Stents have been used to maintain patency in stenosed dialysis access grafts. These stents are typically plain biliary stents. See, e.g., U.S. Pat. No. 5,591,226 (Trerotola et al.) U.S. Pat. No. 5,755,775 (Trerotola et al.), US 2004/0015180 (Yencho et al.) and George X. Zaleski, Brian Funaki, Jordan Rosenblum, Jennifer Theoharis and Jeff Leef, "Metallic Stents Deployed in Synthetic Arteriovenous Hemodialysis Grafts," American Journal of Roentgenology 2001; 176: 1515-1519. (The entire contents of these publications and all other publications mentioned anywhere in this disclosure are hereby incorporated by reference.) Examples of self-expanding stents that have been used in dialysis grafts include the Gianturco Z-stent (Cook) and the Wall Stent (Boston Scientific).

When the dialysis needles are inserted into the graft through the stent they will frequently impact the stent because the stent cell openings are very small. If the needle impacts the stent, it can dislodge it. It can also dull the needle, making it impossible to enter so that the needle has to be removed and reinserted, causing more trauma to the graft. Injury to stents after needle puncture has been observed. See, e.g., Lane et al., "Puncture-Induced Deforming of a Metallic Stent Within a Dialysis Access Graft Causing Thrombotic Failure: Case Report and Description of Salvage," Journal of Vascular and Interventional Radiology 1998; 9:837-839. Lane et al. at page 839, recommends that one refrain from placing needle access in any dialysis graft segment containing a stent. This recommendation is based upon their observation that needle access deforms stents. See also, Rhodes and Silas, "Dialysis Needle Puncture of Wallgrafts Placed in Polytetrafluoroethylene Hemodialysis Grafts," Journal of Vascular and Interventional Radiology 2005 16:1129-1134.

Accordingly, a new method and system for increasing the lives of dialysis grafts are needed.

SUMMARY OF THE INVENTION

Directed to remedying disadvantages in the prior art, disclosed herein is a drug eluting stent construction including a stent having a first end, an opposite second end, a first stent part along a length thereof proximate to the first end and spaced from the second end, and a second stent part along a length thereof proximate to the second end and spaced from the first end. Stent cells in the second part have a Maximum Circular Uncovered Stent Area (MCUSA) greater than stent cells in the first part. A first drug or drug combination is on the first part but not on the second part, and a second different drug or drug combination is on the second part. The first drug or drug combination can include an anti-restenotic drug, and the second different drug or drug combination can include an overlaying anti-thrombotic drug covering both the first part and the second part.

According to another definition of the invention, a stent construction is provided which includes a stent having a first cell pattern proximate to one end of the stent and a second cell pattern proximate to an opposite end of the stent. The first cell pattern has smaller cell dimensions than those of the second cell pattern.

According to a further definition of the present invention, a stent construction is provided which includes a stent having a first end and an opposite second end. The stent has a first zone along a length thereof proximate to the first end and spaced from the second end and a second zone along a length thereof proximate to the second end and spaced from the first end. A first drug or drug combination is on the first zone but not on the second zone, and a second different drug or drug combination is on the second zone. The drugs can be applied to the stent by dip coating, roll coating, electrostatic coating, vapor deposition coating or spray coating.

Pursuant to another embodiment of the present invention, a method is provided which includes positioning a stent construction having a first stent portion adjacent one end thereof and a second stent portion having a different construction than that of the first stent portion adjacent an opposite end thereof at a stenosis at a distal graft-vein anastamosis with the first stent portion adjacent the stenosis. The stent construction can be positioned with the second stent portion adjacent the vein as an arterial venous anastomosis stent, or with the second stent portion adjacent the graft or the vein as a dialysis graft stent.

Other objects and advantages of the present invention will become more apparent to those persons having ordinary skill in the art to which the present invention pertains from the foregoing description taken in conjunction with the accompanying drawings.

DETAILED DESCRIPTION OF PREFERRED EMBODIMENTS OF THE INVENTION

Figure 1:
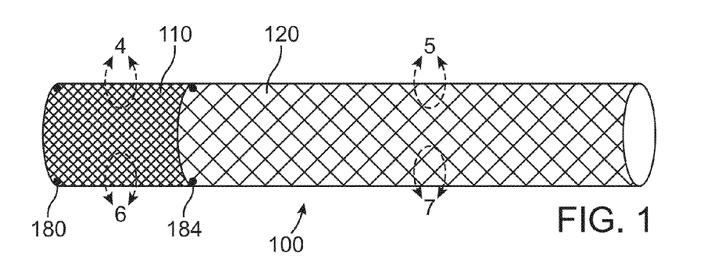
FIG. 1 is an enlarged schematic view of a stent of the present invention having a small cell portion and a large cell portion.

A stent of the present invention is illustrated schematically in FIG. 1, generally at 100, and can be balloon-expandable or self-expandable. As discussed in detail later and with reference to FIGS. 12 and 13, it can be a dialysis graft stent or an arterial venous anastomosis stent. Stent 100, which is preferably formed as a single unitary construction, includes two zones or portions, and can be formed by laser cutting a hypo tube as would be apparent to those skilled in the art from this disclosure. The first portion is shown on the left side of FIG. 1 generally at 110 and a (longer) second portion is shown on the right side generally at 120. The stent 100 can be formed with generally any strut and link configuration as is known. The stent 100, when expanded, can have an internal diameter of between four and eight mm and a length between fifteen and seventy mm, or more particularly, a diameter of approximately six mm and a length of approximately thirty mm.

Figure 12:
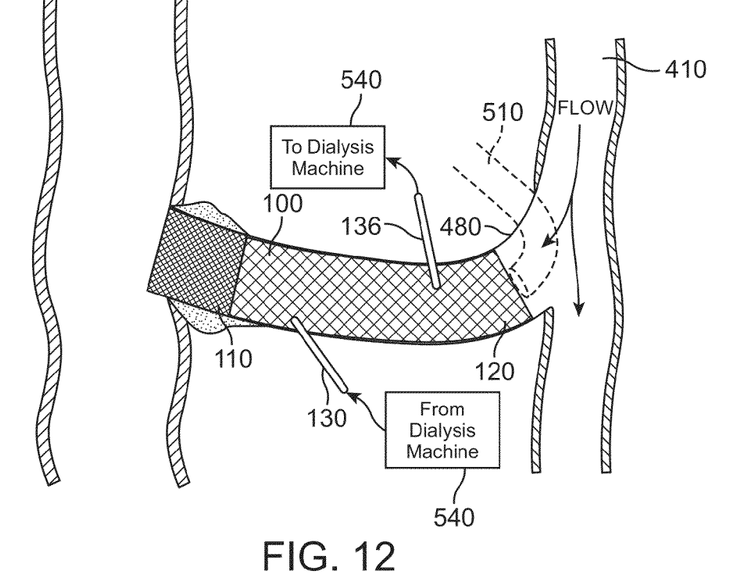
FIG. 12 shows a stent of the present invention in an operative position in the view of FIG. 11.
Figure 13:
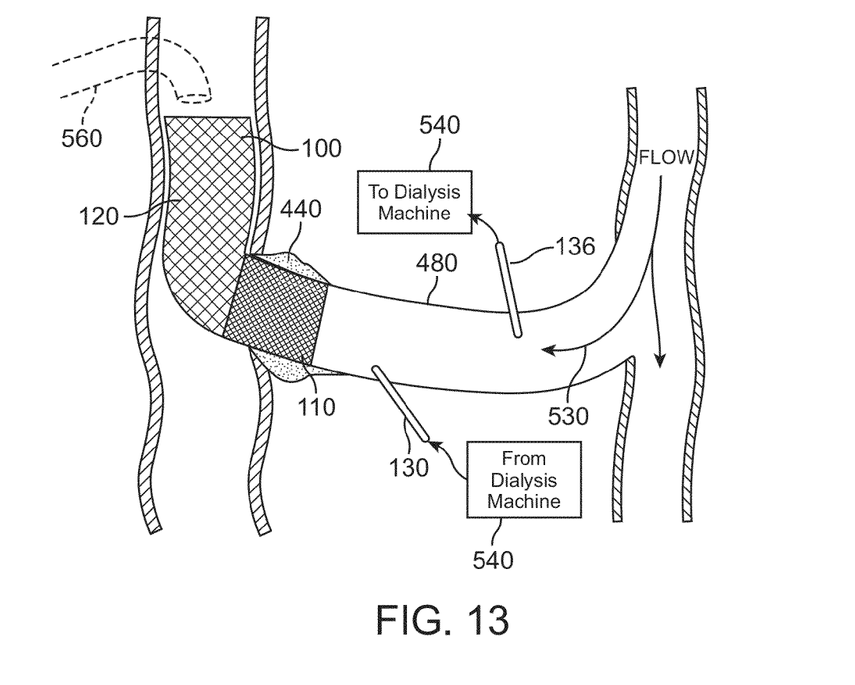
FIG. 13 shows a stent of the present invention in an alternative operative position in the view of FIG. 11.

The first portion 110 has a tighter cell dimension than that of the second portion 120, where the cell dimension is defined by the Maximum Circular Unsupported Surface Area ("MCUSA"). For example, cells in the first portion 110 can have an MCUSA of 2.0 to 5.0 mm$^2$ or approximately 3.5 mm$^2$, while the MCUSA of cells in the second portion 120 can be 6.0 to 80 mm$^2$ or approximately 19.0 mm$^2$. The cells in the second portion 120 are large enough to easily accommodate dialysis needles therethrough such as "14" and "16" Gauge needles, having respective diameters of 1.63 mm and 1.29 mm, and respective cross-sectional areas of 2.09 mm$^2$ and 1.31 mm$^2$. Dialysis needles are shown in FIG(S). 12 (and 13) at 130 and 136.

Today's coronary artery drug eluting stents have maximal circular uncovered surface areas (MCUSA) for individual cells ranging from one to five mm$^2$, which indicates that these cell sizes are acceptable in the drug eluting stent area of the subject stent 100. Areas greater than 2.1 mm$^2$ permit a 14 Gauge needle to penetrate with only a low probability of touching the stent. The probability of introducing a 14 Gauge needle without touching the stent increases as the areas of the individual cells increase, with areas of at least five mm$^2$ being acceptable.

The first portion 110 has cells 140 having a smaller MCUSA than that of the cells 142 of the second portion 120 so that the first portion can hold and effectively transmit drugs from a coating 148 to the anastomotic stenosis, as shown in FIG. 12 for example. These drugs are lipophilic so the cell size needs to be small to provide drug to the entire area to prevent hyperplasia from occurring, which creates restenosis. The second portion 120 can have a different drug coating 150 for transmitting drugs into the bloodstream. Blood clot formation in grafts is a problem and can be exacerbated by the presence of the stent, a foreign body. Accordingly, an anti-thrombotic drug can be provided throughout the entire length of the stent 100 or at least in the non-drug eluting stent area 120. A purpose of the anti-thrombotic coating is thus to reduce the likelihood of thrombosis being initiated by the stent 100. This is especially true for metallic stents made of materials such as stainless steel, cobalt chrome, and nitinol. Furthermore, thrombosis is exacerbated by stents damaged by needle penetration, suggesting that an anti-thrombotic coating can retard that thrombosis.

Figure 4:
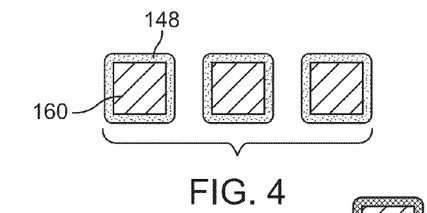
FIG. 4 is an enlarged view taken on circle 4 of FIG. 1 showing the coating on the struts in the small cell portion.
Figure 5:
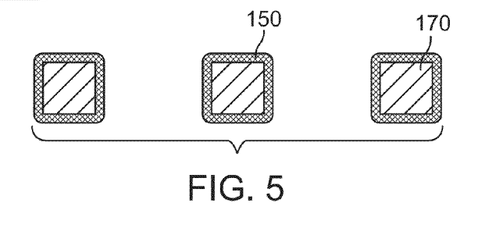
FIG. 5 is an enlarged view taken on circle 5 of FIG. 1 showing the coating on the struts in the large cell portion.

The drug of the first portion 110 is shown coated on struts 160 of the first portion in FIG. 4. FIG. 5 shows struts 170 in the cell pattern of the second portion 120 coated with a different second drug 150. While the struts 160, 170 are illustrated as having rectangular cross-sections, other shapes as would be apparent to those skilled in the art can be used. Further, the struts within the same stent can have different widths.

The first stent portion 110 can have an anti-restenotic drug coating 148. The drug of this coating can be eluted from a nonabsorbable or absorbable polymer placed on a metallic stent or eluted from a stent composed of a mixture of a bioabsorbable polymer and drug or drugs. Biocompatible, nonabsorbable polymers include alkylene vinyl alcohol copolymers such as ethylene vinyl acetate (EVA), alkylene vinyl alcohol copolymers such as ethylene vinyl alcohol (EVAL), poly (n-butyl methacrylate (PMBA), SOLEF polymers such as poly (vinylidene fluoride-co-hexafluoropropene (PVDF-co-HFP and poly (vinylidene fluoride) (PVDF) and combinations thereof. Biocompatible, bioabsorbable polymers include blends of polyesters, poly (D,L-lactide), poly (L-lactide), polyglycolide, and poly (D,L-lactide-co-glycolide). See U.S. Pat. No. 6,673,385 (Ding et al.) and US 2004/0086542 (Hossainy et al.).

The anti-restenotic drug can be a single drug or a combination of drugs that are eluted at similar or different rates. The drugs include but are not limited to: (1) antiproliferative drugs such as everolimus, sirolimus, ABT-578, and paclitaxel; (2) anti-inflammatory drugs such as corticosteroids (e.g., clobetasol, dexamethasone, and momentasone), inhibitors of the NFkB and p38 pathways; (3) immunosuppressants such as tacrolimus and pimecrolimus; and (4) pro-healing drugs such as 17-beta estradiol, nitric oxide donors, and nitric oxide generators (e.g., chelated copper catalysts).

The struts 170 of the second stent portion 120 can have an anti-thrombotic coating 150 as mentioned above especially on the luminal surfaces thereof. This coating 150 can include: (1) anti-thrombotics including heparan or heparin; and (2) antiplatelet drugs including nitric oxide donors or nitric oxide generators (chelated copper catalysts).

More particularly, the first drug or drug combination can include an anti-restenotic drug and the second different drug or drug combination can include an overlaying anti-thrombotic drug covering both the first zone or portion 110 and the second zone or portion 120. See U.S. 2005/0192662 (Ward). The drugs can be applied by techniques known in the art including spray coating, dip coating and roll coating. Another coating application technique uses "depot" technology (see, e.g., US 2005/0234544 (Shanley)), or applies the coating in channels or grooves on the stent surfaces.

Figure 2:
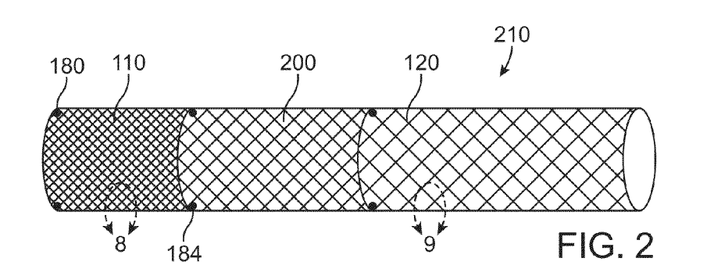
FIG. 2 is a view of a first alternative of the stent of FIG. 1.
Figure 3:
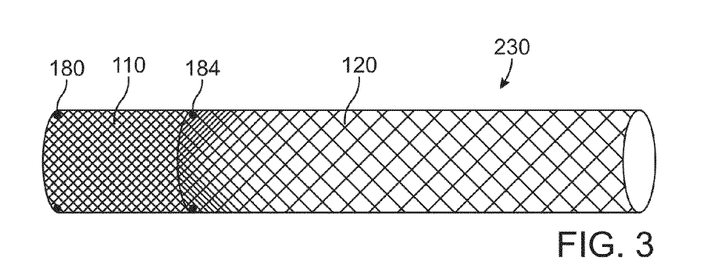
FIG. 3 is a view of a second alternative of the stent of FIG. 1.

To assist in the placement of the strut in the body, radiopaque markers 180, 184 are provided at opposite ends of the first portion. These (metal) radiopaque markers can have a construction as is known in the prior art, for biodegradable stents. The markers can also be provided at the opposite end of the stent 110, that is, at the right end of FIG(S). 1 (and 2 and 3).

It may be to reduce the effect of bending stresses at the juncture of the first and second portions 110, 120, that a transitional portion 200 can be provided therebetween as shown in FIG. 2 for the first alternative stent 210. The transitional portion 200 can have a cell pattern with cells having an MCUSA greater than those of the first portion 110 but smaller than those of the second portion 120. Alternatively, the second portion 120 can have a gradually increasing MCUSA for cells at the end adjacent the first portion 110 to the opposite end 220, as illustrated in FIG. 3 by the second alternative stent 230.

Figures 6, 7, 8, 9:
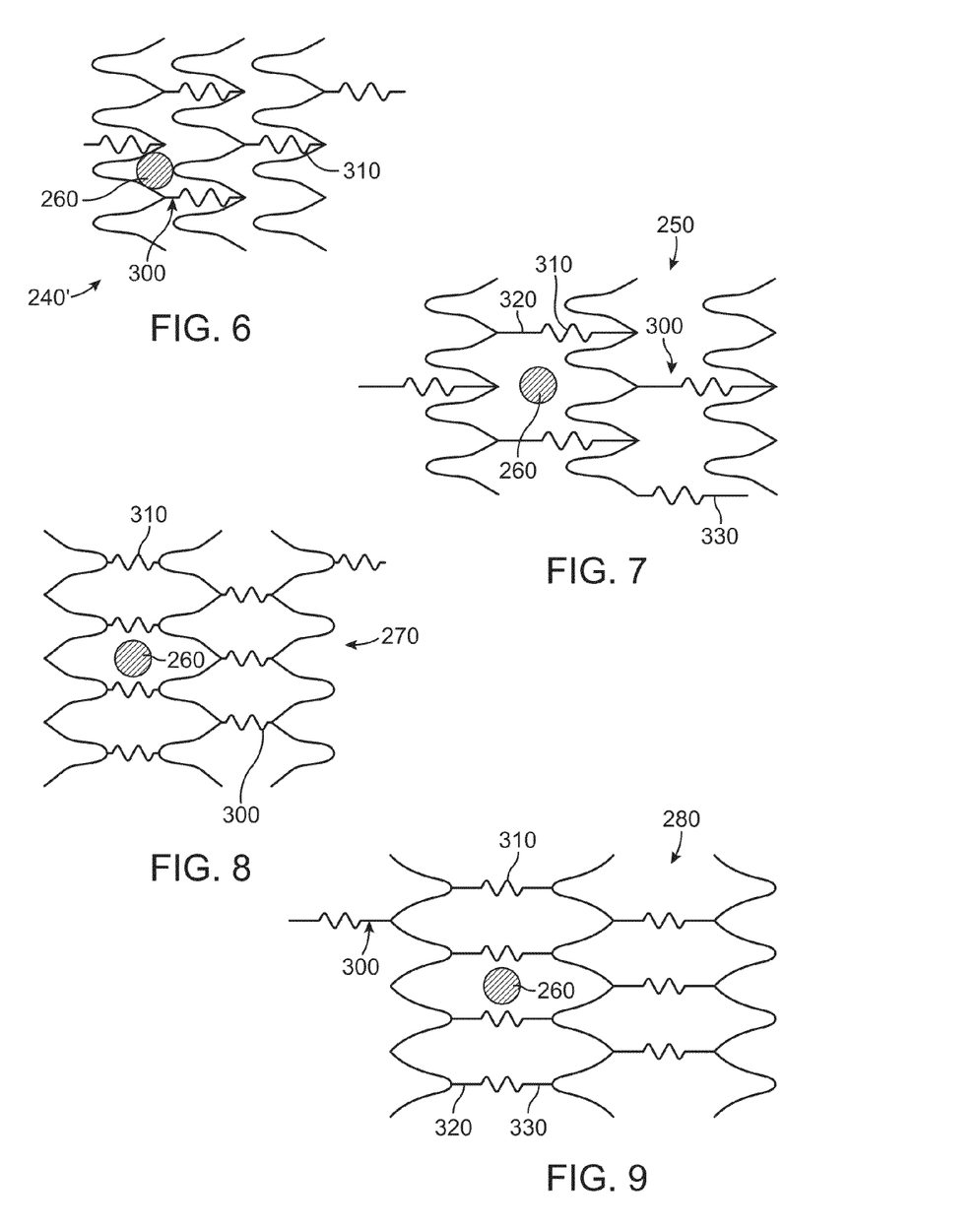
FIG. 6 is an enlarged view taken on circle 6 of FIG. 1 showing a small open-cell layout with a dialysis needle illustrated.
FIG. 7 is an enlarged view taken on circle 7 of FIG. 1 showing a large open-cell layout with a dialysis needle illustrated.
FIG. 8 is an enlarged view taken on circle 8 of FIG. 2 showing a small closed-cell layout with a dialysis needle illustrated.
FIG. 9 is an enlarged view taken on circle 9 of FIG. 2 showing a large closed-cell layout with a dialysis needle illustrated.
Figure 10:
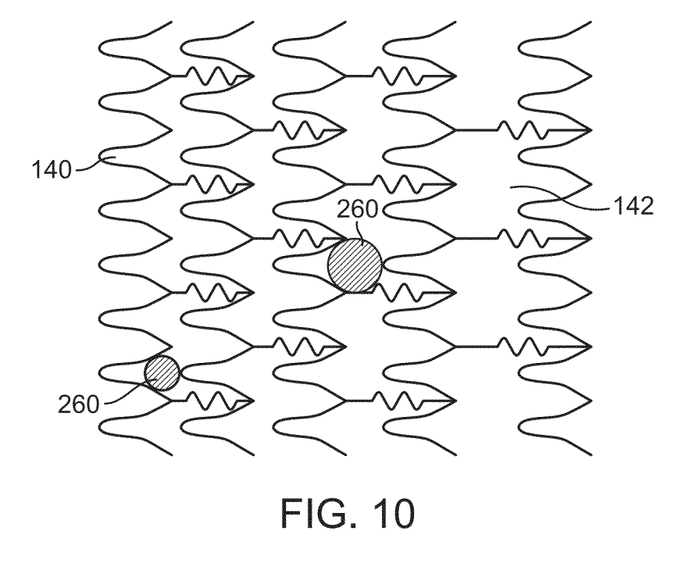
FIG. 10 is an enlarged view taken at the intersection of the small cell portion and the large cell portion of the stent of FIG. 1 showing the maximum circular unsupported surface areas (MCUSA) for both portions.

The patterns of the cells 140 of the first stent portion 110 and/or the cells 142 of the second stent portion 120 can have an "open" cell construction such as illustrated in FIG. 6 as well as in FIG. 7. Examples of open cell designs are those of the RX Herculink Plus stent and the Multi-Link Zeta stent. While FIG. 6 shows at 240 a small open cell construction with a small MCUSA, FIG. 7 shows at 250 a large open cell construction with a large MCUSA. The relative sizes can be understood from the cross-section of the dialysis needle 260 drawn in these figures. Alternatively, the first portion 110 and/or the second portion 120 can have a closed cell construction, such as illustrated in FIGS. 8 and 9. FIG. 8 shows at 270 a small closed cell layout, and FIG. 9 shows a large closed cell layout at 280 with a larger MCUSA than that of the layout 270. Examples of closed cell designs are the Palmax Genesis stent and the Cypher Sirolimus-Eluting Coronary stent.

The stent cell size can be increased by increasing the distance between the struts, as can be seen from comparing FIG. 6 with FIG. 7, and FIG. 8 with FIG. 9. Alternatively, it can be increased by switching from a closed cell design to an open cell design by eliminating a link, as can be understood from comparing FIGS. 8 and 9 with FIGS. 6 and 7. See, e.g., Garasic, J Metal., Circulation 101: 812-818, 2000. To increase the MCUSA of the open and/or closed cell configurations, the length of the strut links 300 can be increased. If the links 300 have undulations 310, one way of increasing the lengths of the links is to increase the lengths of the undulations 310. Another way is to increase the number of undulations 310 per link 300. A third way is to increase the lengths of the straight portions 320, 330 on one or both sides of the undulations 310 as can be seen by comparing FIGS. 6 and 7 and by comparing FIGS. 8 and 9.

The stent 100, for example, can have a strut and link configuration as disclosed in U.S. Pat. No. 6,616,689 (Ainsworth et al). The links 300 of the second portion 120 can each be approximately two to six mm long, and the links 300 of the first portion 110 can each be approximately one to three mm long. Alternatively, the links 300 of the second portion 120 can be approximately one to five mm longer than the links of the first portion 110. Another definition of the invention is for the links 100 in the first cell portion 110 to have lengths which provide MCUSA's of two to five $mm^2$ of the cells 140 in the first portion 100, when expanded. Links 300 in the second cell portion 120 can have lengths which provide MCUSA's of six to eighty $mm^2$ of cells 142 in the second portion of the stent 100 when expanded. Alternatively, the links 300 can have lengths which provide MCUSA's of approximately 3.5 $mm^2$ in the first portion 110 of the stent 100 when expanded and the links in the second portion 120 can have lengths which provide MCUSA's of approximately 19 $mm^2$ in the second portion of the stent when the stent is expanded. In other words, the short links (as on the left portion of FIG. 1, for example) would be in the area of the stent that would contain the drug and would be placed at the graft vein anastamoses, as depicted in FIGS. 12 and 13.

The underlying stent 100 itself can be made of a biodegradable metal or polymer. Examples of biocompatible, bioabsorbable polymers include blends of polyesters, poly (D,L-lactide), poly (L-lactide), polyglycolide, poly (D,L-lactide-co-glycolide), poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g., PEO/PLA), polyphosphazenes, biomolecules (such as fibrin, fibrinogen, cellulose, starch, collagen and hyaluronic acid), polyphosphoester, polyphosphoester urethane, poly(amino acids), cyanoacrylates, and poly(iminocarbonate) polydioxanone. Examples of usable biodegradable metals for the stent 100 include magnesium alloys such as an alloy of, magnesium, yttrium and rare earth, and usable bioerodible metals include magnesium, zinc, and iron. The underlying stents can be metal stents or polymer stents; they can be bioabsorbable, bioerodable, and/or biodegradable polymeric stents with or without metallic components. Metals including cobalt chromium alloy (Elgiloy), stainless steel (316L), Nitinol, tantalum, and nickel-titanium alloy can be used as the stent material.

The first portion 110 of the stent 100 can be shorter than the second portion 120. It can be approximately one-third of the length of the total stent 100, while the second portion can be two-thirds of the length. Alternatively, the first portion 110 can have a stent length approximately between twenty and fifty percent of the length of the stent 100, and the second portion 120 can have a length approximately between fifty and eighty percent of the length of the stent. As an example, the stent 100, when expanded, can have an internal diameter of between four and eight mm and a length between fifteen and seventy mm, or more specifically a diameter of approximately six mm and a length of approximately thirty mm.

Figure 11:
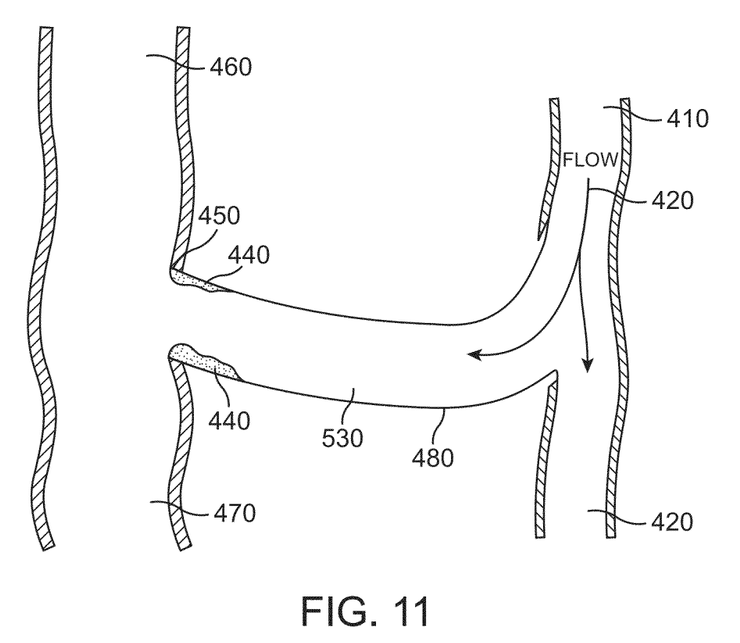
FIG. 11 is a schematic view of a stenosis at a distal graft-vein anastomosis.

FIG. 11 shows a stenosis at a distal graft-vein anastomosis. Referring to the reference numerals in that figure, disclosed therein are proximal artery 410, blood flow 420, distal artery 430, stenosis 440, distal anastomosis 450, central vein 460, distal vein 470, and (PTFE) graft 480.

The stent 100 can be used as a dialysis graft stent as shown in FIG. 12. The catheter for inserting the stent 100 in position as shown in FIG. 12 is illustrated in phantom lines at 510 on the right side of the drawing. A first dialysis needle 130 can be inserted through the graft 480 and a first stent cell in the second stent portion 120 and into the blood channel 530 in the graft; and a second dialysis needle 136 can be inserted through the graft 520 and a second stent cell in the second stent portion 120, or through the graft 520 directly into the blood channel 530 in the graft. Blood from the blood channel 530 at a proximal area is withdrawn through the inserted first dialysis needle 136, processed in a dialysis machine 540, and returned through the inserted second dialysis needle into the blood channel at a distal area thereof.

Alternatively, the stent 100 can be used as an arterial venous anastomosis stent as shown in FIG. 13. The catheter for inserting the stent in the position of FIG. 13 is illustrated in the upper left portion of that figure in phantom lines at 560. Both of the dialysis needles 136, 130 pass directly in the graft

480, and not through the stent 110, and into the blood channel 530. The open cell design is useful in this alternative placement of the stent even though the dialysis needles 130, 136 will not be inserted through the cells in this embodiment for two reasons. First, venous flow can go through more easily because it is less restricted. Second, because of the anti-thrombotic coating, there is reduced likelihood of thrombosis in the venous segment.

In summary, the present invention can include a self-expanding or balloon-expandable stent comprised of nitinol or biodegradable polymer and having two cell patterns. An open cell pattern in the area proximal to the anastamosis is provided in order to facilitate needle punctures of the (PTFE) graft. The performance of this area can be further enhanced by rounding the edges of the stent struts to better deflect needles that strike the strut. The stent has a less open pattern in the area that would be opposed to the anastamotic area. This tighter cell design enhances drug delivery by providing additional surface onto or into which drugs can be placed. In addition, it decreases diffusion distances and thereby decreases the likelihood that there would be areas unaffected by the drug.

Another definition of the invention is a drug coated stent in which the area in contact with the PTFE graft is coated with a polymer that is nonfouling or anti-thrombotic or has affixed to it or elutes a drug that prevents/inhibits thrombosis. An example is a hydrogel to which is tethered a heparin or nitric oxide donor/generator. The closed cell area of the stent that is in contact with the stenotic vein-graft anastamosis elutes a drug that inhibits restenosis. The drug can be a single drug such as everolimus of paclitaxel, or a drug combination such as everolimus with a anticoagulant/antithrombotic; everolimus with a nitric oxide donor/generator; everolimus with an anti-inflammatory; or everolimus with an immunosuppressant. This area may also be coated with an antifouling coating that prevents clot formation.

The stent is designed to be deployed via a catheter inserted directly through the dialysis graft material or via an artery or vein that leads to or from the graft. The small cell region of the stent can be positioned at the site of the anastamotic stenosis. The large cell region of the stent can be positioned in the graft area. The biodegradable polymer can be one that has a property to self-expand to bring the drug eluting portion of the device in contact with the anastamotic stenosis and then degrade faster than the graft is expected to fail. This advantageously permits another such stent to be inserted before the graft occludes.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. A stent construction, comprising:
    a stent forming a bore and including a first cell pattern at one end of the stent and a second cell pattern at an opposite end of the stent, wherein each cell of the first cell pattern contains a first maximum circular area, each cell of the second cell pattern contains a second maximum circular area, and the second maximum circular area is larger than the first maximum circular area;
    the first cell pattern extending from the one end to about 20% to 50% of the total stent length; and
    a first drug carried on a first surface defined by the first cell pattern;
    wherein the about 20% to 50% of the total stent length carrying the first drug enables the stent to deliver an efficacious amount of the first drug to a vessel area; and
    wherein the remaining about 80% to 50%, respectively, of the total stent length is occupied substantially by the second cell pattern;
    a second drug carried on a second surface defined by the second cell pattern;
    wherein the first drug is not on the second surface and the second drug is not on the first surface;
    wherein the second cell pattern enables a dialysis needle to penetrate a graft supported by the stent and enter the stent bore by way of the second cell pattern with a substantially lower probability of damaging the stent than if the dialysis needle were to penetrate the graft and enter the stent bore by way of the first cell pattern.

2. The construction of claim 1 wherein the stent is a self-expanding stent.

3. The construction of claim 1 wherein the stent is a balloon-expandable stent.

4. The construction of claim 1 wherein the first cell pattern includes first stent links and the second cell pattern includes second stent links, the second stent links being longer than the first stent links.

5. The construction of claim 4 wherein the first stent links have first undulations between link ends thereof, and the second stent links have second undulations between link ends thereof; and wherein the number of second undulations of each of the second stent links is greater than the number of first undulations of each of the first stent links, or wherein the second undulations are each longer than the corresponding first undulations.

6. The construction of claim 4 wherein the first stent links have lengths which provide a maximum circular area of approximately 3.5 mm$^2$ in the first cell pattern of the stent when expanded and the second stent links have lengths which provide a maximum circular area of approximately 19 mm$^2$ in the second cell pattern of the stent when expanded.

7. The construction of claim 1 wherein the cells of the first cell pattern and the cells of the second cell pattern are all open cells or are all closed cells.

8. The construction of claim 1 wherein each of the cells of the second cell pattern has a maximum circular area at least five mm$^2$ greater than that of the cells of the first cell pattern.

9. The construction of claim 1 wherein cells in the first cell pattern are closed cells and cells in the second cell pattern are open cells, or wherein cells in the first cell pattern are open cells and cells in the second cell pattern are closed cells.

10. The construction of claim 1 wherein the stent is made of biodegradable polymer or metal.

11. The construction of claim 1 further comprising an anti-thrombotic coating on at least luminal surfaces of the second cell pattern, and wherein the anti-thrombotic coating is also on at least luminal surfaces of the first cell pattern.

12. The construction of claim 1 wherein the second cell pattern has a stent length longer than that of the first cell pattern.

13. The construction of claim 1 wherein the first drug is an anti-restenotic drug and the second drug is an anti-thrombotic drug.

14. The construction of claim 1 wherein the first cell pattern occupies about 33% of the total stent length.

15. The construction of claim 14, wherein the second cell pattern occupies about 66% of the total stent length.

16. The construction of claim 1, wherein the second cell pattern occupies about 66% of the total stent length.

17. A stent construction, comprising:
a stent having a first end and an opposite second end and defining a lumen;
the stent having a first stent zone extending from the first end and spaced from the second end and a second stent zone extending from the second end and spaced from the first end the first and second stent zones defining cells,
wherein each one of the cells in the first stent zone defines an open space that contains a first maximum circular area and each one of the cells in the second stent zone defines an open space that contains a second maximum circular area, the first maximum circular area being smaller than the second maximum circular area;
an anti-restenosis drug or drug combination along the entire length of the first zone but not on the second zone; and
an anti-thrombotic drug or drug combination along the entire length of the second zone but not the first zone;
wherein the stent has a length measured as the distance between the first and second ends and the first stent zone occupies from 20% up to about 50% of the stent length;
wherein the first stent zone occupying 20% up to about 50% of the total stent length sufficiently holds and effectively transmits the anti-restenosis drug or drug combination to the vessel while a sufficient portion of the total stent length remains for allowing a dialysis needle to be frequently penetrated through the second stent zone and into the stent lumen.

18. The construction of claim 17 wherein the first maximum circular area is two to five mm² and the second maximum circular area is six to eighty mm².

19. The construction of claim 17 wherein the first maximum circular area is approximately 3.5 mm² and the second maximum circular area is approximately 19 mm².

20. The construction of claim 17 wherein the stent is a biodegradable stent.

21. The construction of claim 17 wherein the anti-restenotic drug is on at least abluminal surfaces of the first zone, and the anti-thrombotic drug is on at least luminal surfaces of the second zone.

22. The construction of claim 17 wherein the stent construction is a dialysis graft stent construction or is an arterial venous anastomosis stent construction.

23. The construction of claim 17 wherein the first zone has a length of one to three cm, the second zone has a length of two to six cm and the stent has a length of four to eight cm, or wherein the first zone has a length of approximately two cm, the second zone has a length of approximately four cm and the stent has a length of approximately six cm.

24. A dialysis graft kit, comprising:
a graft for being connected to a vessel; and
a stent for supporting the graft when the graft is connected to the vessel, the stent comprising:
a first end and an opposite second end,
the stent having a first stent zone extending from the first end and spaced from the second end and a second stent zone extending from the second end and spaced from the first end,
wherein when the stent is expanded within the graft and supports the graft, each of the cells in the first stent zone define an open space that contains a first maximum circular area and each of the cells in the second stent zone define an open space that contains a second maximum circular area, the first maximum circular area being smaller than the second maximum circular area,
the first stent zone occupies about 33% of the stent length,
the second stent zone occupies about 66% of the stent length, and
a first drug or drug combination along the entire length of the first zone but not on the second zone, and a second drug or drug combination along the entire length of the second zone but not the first zone.

* * * * *

UNITED STATES PATENT AND TRADEMARK OFFICE
CERTIFICATE OF CORRECTION

PATENT NO.        : 8,518,100 B2                                   Page 1 of 1
APPLICATION NO.   : 11/312159
DATED             : August 27, 2013
INVENTOR(S)       : Consigny et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 722 days.

Signed and Sealed this
Twenty-fourth Day of March, 2015

Michelle K. Lee
*Director of the United States Patent and Trademark Office*